US006149641A

United States Patent [19]

Ungs

[11] Patent Number: 6,149,641

[45] Date of Patent: *Nov. 21, 2000

[54] LOCAL DELIVERY OF ESTROGEN FOR ANGIOGENESIS

[75] Inventor: Mark T. Ungs, St. Paul, Minn.

[73] Assignee: SciMed Life Systems, Inc., Maple Grove, Minn.

[ * ] Notice: This patent is subject to a terminal disclaimer.

[21] Appl. No.: 09/220,985

[22] Filed: Dec. 23, 1998

Related U.S. Application Data

[63] Continuation of application No. 08/916,430, Aug. 21, 1997, Pat. No. 5,866,561.

[51] Int. Cl.[7] .......... A61N 1/30

[52] U.S. Cl. .......... 604/501; 604/507; 604/103.01; 604/103.02; 623/1

[58] Field of Search .......... 623/1; 604/21, 604/506–510, 501, 103.01–103.02

[56] References Cited

U.S. PATENT DOCUMENTS

| | | | |
|---|---|---|---|
| 5,180,366 | 1/1993 | Woods | 604/96 |
| 5,219,739 | 6/1993 | Tischer et al. | 435/69.4 |
| 5,295,962 | 3/1994 | Crocker et al. | 604/101 |
| 5,300,679 | 4/1994 | Baylis et al. | 562/11 |
| 5,376,652 | 12/1994 | Javitt | 514/177 |
| 5,389,314 | 2/1995 | Wang | 264/25 |
| 5,395,831 | 3/1995 | Gemmill, Jr. et al. | 514/179 |
| 5,425,703 | 6/1995 | Feiring | 604/21 |
| 5,437,864 | 8/1995 | Edgington et al. | 424/145.1 |
| 5,457,113 | 10/1995 | Cullinan et al. | 514/319 |
| 5,462,937 | 10/1995 | Cullinan et al. | 514/212 |
| 5,472,985 | 12/1995 | Grainger et al. | 514/651 |
| 5,492,926 | 2/1996 | Cullinan et al. | 514/422 |
| 5,516,528 | 5/1996 | Hughes et al. | 424/464 |
| 5,538,504 | 7/1996 | Linden et al. | 604/53 |
| 5,545,569 | 8/1996 | Grainger et al. | 436/518 |
| 5,552,395 | 9/1996 | Gemmill, Jr. et al. | 514/179 |
| 5,554,119 | 9/1996 | Harrison et al. | 604/96 |
| 5,567,828 | 10/1996 | Dodge | 549/51 |
| 5,580,569 | 12/1996 | Giampapa | 424/426 |
| 5,580,722 | 12/1996 | Foulkes et al. | 435/6 |
| 5,591,129 | 1/1997 | Shoup et al. | 604/96 |
| 5,882,334 | 3/1999 | Sepetka . | |
| 6,045,565 | 4/2000 | Ellis et al. . | |

FOREIGN PATENT DOCUMENTS

| | | |
|---|---|---|
| WO 97/19697 | 6/1997 | WIPO . |

OTHER PUBLICATIONS

Hyder, et al., "Triphenylethylene Antiestrogens Induce Uterine Vascular Endothelial Growth Factor Expression Via Their Partial Estrogen Agonist Activity," *Cancer Lett.* (Shannon, Irel.), 120 (2), pp. 165–171 (1997). (Abstract).

Morales, et al., "Estrogen Promotes Angiogenic Activity In Human Umbilical Vein Endotheilal Cells in Vitro And In A Murine Model," *Circulation*, 91 (3), pp. 755–763 (1995). (Abstract).

*Textbook of Biochemistry with Clinical Correlations*, Edited by Thomas M. Devlin, PhD., Wiley–Liss Publications, Copyright 1992, p. 921.

*The Encyclopedia of Molecular Biology*, Sir John Kendrew, Blackwall Science, Copyright 1994, p. 1112.

Bruengger et al., "Smooth Muscle Cell of the Canine Prostate in Spontaneous Benign Hyperplasia, Steroid Induced Hyperplasia and Estrogen of Tamoxifen Treated Dogs", *The Journal of Urology*, vol. 130, Dec. 1983, pp. 1208–1210.

Schwartz et al., "Nicotinic Cholinergic Receptor Binding Sites in the Brain: Regulation in vivo", *Science*, vol. 220, No. 4593, Apr. 1983, pp. 214–216.

*Primary Examiner*—Mark Bockelman
*Attorney, Agent, or Firm*—Crompton, Seager & Tufte, LLC

[57] ABSTRACT

A method for inducing angiogenesis in blood vessels proximal to ischemic tissue or proximal to stenosed regions including application of an estrogen compound to the blood vessel walls at a treatment site proximal to or upstream of the stenosis. A preferred delivery device is a double walled drug delivery catheter having porous outer walls. Another suitable delivery device is a drug injection device for injecting angiogenic material into blood vessel walls. One delivery method utilizes iontophoresis.

11 Claims, 1 Drawing Sheet

LOCAL DELIVERY OF ESTROGEN FOR ANGIOGENESIS

This application is a continuation of U.S. patent application Ser. No. 08/916,430, filed Aug. 21, 1997 now U.S. Pat. No. 5,866,561.

FIELD OF THE INVENTION

The invention relates generally to a method for inducing angiogenesis upstream of blood vessel occlusions. More specifically, the invention relates to applying estrogen compounds to blood vessel regions to induce angiogenesis upstream of ischemic tissue.

BACKGROUND OF THE INVENTION

Arteriosclerosis and the resulting myocardial infarction is a leading cause of death, particularly in males. Percutaneous Transluminal Coronary Angioplasty (PTCA) is one treatment used to treat patients with coronary artery disease. PTCA can relieve myocardial ischemia by dilating lumen obstructions, thereby increasing coronary blood flow. Unfortunately, restenosis following PTCA is a significant problem, occurring about 30% of the time within 6 months. Various treatments have been suggested to deal with restenosis.

Administration of compounds for inhibiting vascular smooth muscle cell proliferation and restenosis has been suggested by Cullinan et al. (U.S. Pat. No. 5,462,937). Woods (U.S. Pat. No. 5,180,366) discloses an application of smooth muscle cell anti-proliferation agents, including estrogen, and endothelial growth factor to inhibit restenosis has also been suggested. Growth and division of endothelial cells was said to be promoted while proliferation of smooth muscle cells was believed to be inhibited.

Application of Vascular Endothelial Growth Factor (VEGF) as a post-operative wound healing agent after balloon angioplasty has been suggested, in an amount effective to promote endothelial cell growth by Tischer et al. (U.S. Pat. No. 5,219,739). Inhibition of smooth muscle cell proliferation by administration of an effective amount of Transforming Growth Factor-beta activators or production simulators that act to inhibit vascular smooth muscle cell proliferation has also been proposed by Grainger et al. (U.S. Pat. No. 5,472,985).

It is believed that the more common occurence of restenosis in men compared to women suggests hormones play a role. Oral, transdermal, and implant delivery administration of a therapeutically effective amount of estrogen has been suggested as a method for reducing the risk of heart disease by Hughes et al. (U.S. Pat. No. 5,516,528). A method for reducing restenosis by administering estrogen in a dose sufficient to stimulate synthesis of 27-hydroxychloresterol in the vascular endothelium tissue has also been proposed by Javitt (U.S. Pat. No. 5,376,652). Administration of estrogen to the stenosed, dilated region after PTCA has thus been suggested for the purposes of preventing restenosis.

PTCA is not always a successful solution or even a viable treatment option, as not all stenosed regions can be treated with PTCA. For example, some regions are unreachable with the required size high pressure balloon, which must be advanced through the narrowed, occluded vessel region. Some stenoses are totally blocked, denying entry to a dilitation catheter attempting to advance within. Other vessel regions are too narrow or geometrically too tortuous for dilitation. Damage to weakened vessel walls is a possibility during balloon inflation as well, and may preclude PTCA in some cases. Treatment to increase perfusion to heart tissue, in place of, or in addition to, PTCA would be desirable.

SUMMARY OF THE INVENTION

The present invention provides a method for increasing circulation to heart tissue involving the application of estrogen compounds to blood vessel walls to promote angiogenesis. Applicants believe estrogen induces angiogenesis (blood vessel growth) and increases permeability. This provides increased local blood circulation through neovascularization, the creation of new blood vessels.

A preferred location for application of the estrogen is proximal to, or upstream of, ischemic tissue or a stenosis. This creates new blood vessels proximal to the ischemic tissue or a stenosis. The invention is relatively more beneficial when practiced in smaller blood vessels when it is considered that smaller vessels are the vessels more likely to present difficulties in being crossed with balloon catheters and dilated, while also being the vessels which supply blood to a smaller area of tissue which is believed benefited most from angiogenesis.

One method of delivering the angiogenesis inducing compound or estrogen compound includes application with a double walled drug delivery balloon catheter having a porous outer wall. A preferred catheter is a perfusion balloon catheter. The balloon can be advanced to a site proximal the ischemic tissue or stenosis, the inner balloon inflated, bringing the outer balloon into close contact with the blood vessel wall. The compound can then be injected into the catheter lumen, thereafter flowing into the space between the balloon walls, and out to contact the vessel walls.

In yet another embodiment, a balloon envelope is coated with a viscous or otherwise difficult to inject estrogen containing compound. The balloon envelope and a sheath are advanced co-extensively until reaching the treatment site, the sheath withdrawn, and the balloon expanded, forcing the compound against the vessel wall.

Another method of delivering the estrogen compound includes use of iontophoresis. A delivery balloon releases the compound within the vessel, where the compound is ionic or can be carried along with an ionic material. Electrodes external to the patients body are used to create an electric field which acts as a driving force to cause molecules to advance toward an oppositely charged pole.

Yet another method of compound delivery includes advancing a drug delivery catheter having a puncturing element to the delivery site. The puncturing element is moved to puncturing position, the inner wall punctured, and the compound injected into the vessel wall. An estrogen compound could also be coated on a stent and placed at a desired delivery site, temporarily or permanently.

DETAILED DESCRIPTION OF THE PREFERRED EMBODIMENTS

A preferred method of estrogen compound material delivery includes inflating a balloon having an estrogen compound covering a substantial portion of the balloon. The compound is thus held in place against the vessel wall, promoting adsorption through the vessel wall. A preferred catheter for delivery is a perfusion balloon catheter. A catheter allowing perfusion therethrough allows holding the estrogen compound against the vessel walls for longer adsorption times while allowing blood to-flow through the blood vessel. Examples of catheters suitable for estrogen compound application are drug delivery catheters as disclosed in U.S. Pat. No. 5,558,642, entitled “Drug Delivery Catheter” or U.S. Pat. No. 5,554,119, entitled “Drug Delivery Catheter with Manifold”, the disclosures of which are incorporated herein by reference. Another suitable catheter is disclosed in U.S. patent application Ser. No. 08/441,168, filed May 15, 1995, entitled “Perfusion Balloon Angioplasty Catheter” now abandoned to the present assignee, the disclosure of which is incorporated herein by reference. This disclosed catheter can be constructed with a porous drug delivery member over the balloon, as illustrated in FIG. 1.

Figure 1:
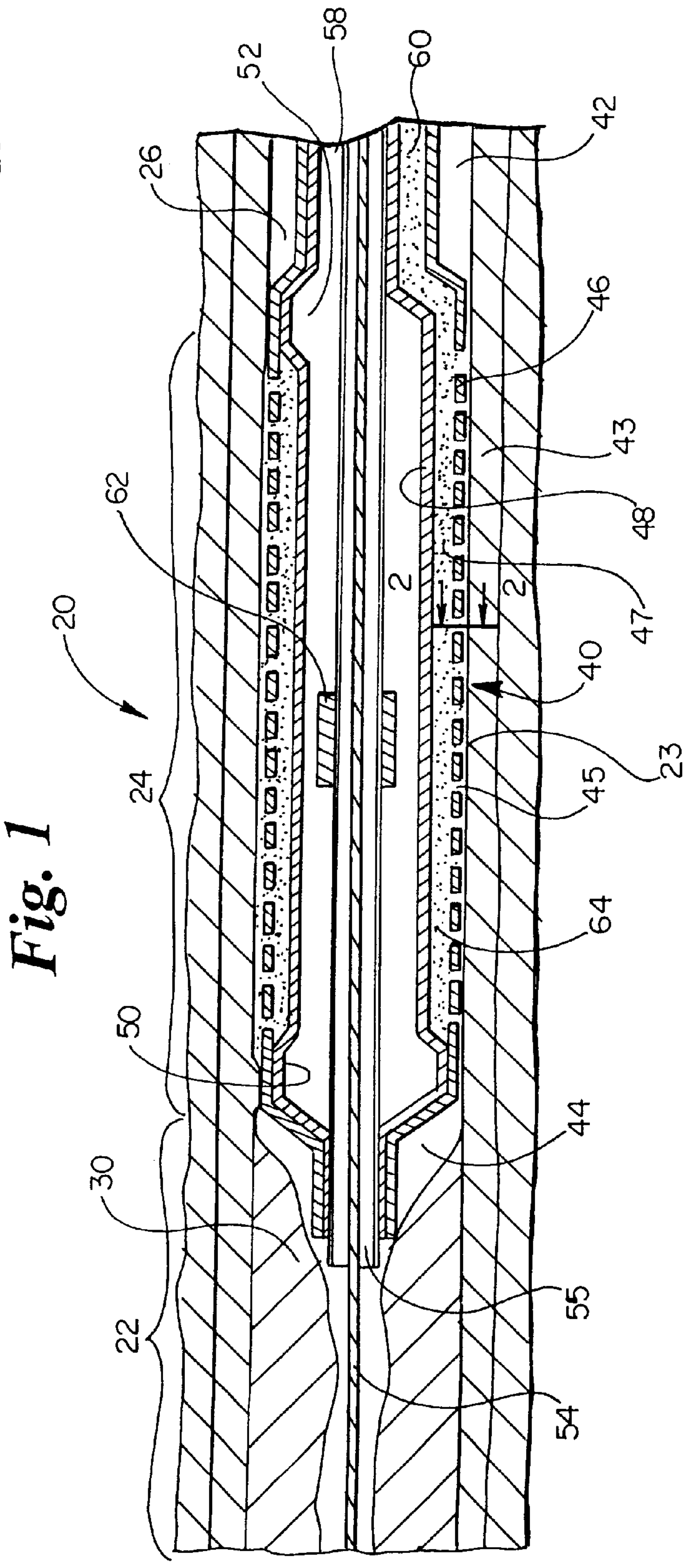
FIG. 1 is a fragmentary side elevational view of a stenosed vessel sectioned vertically on the vessel longitudinal axis and having an estrogen, compound applying catheter proximally thereof.

FIG. 1 illustrates a blood vessel 20 having an inner wall 23, a lumen 26 and stenosed region 30 and a more proximal region 24, where stenosed region 22 is more occluded and proximal region 24 is less occluded. Stenosed region 22 includes a stenosis 33 within as representative of an area of ischemic tissue. A compound delivery device 40 is illustrated, here double walled balloon catheter 40, inserted to a treatment site in vessel lumen 26 proximal to or upstream of stenosed region 22. Catheter 40 has a balloon 43 extending from balloon proximal end 42 to balloon distal end 44. Balloon 43 includes an inner envelope 48 and an outer, porous envelope 46. An interior space 47 lies between inner envelope 48 and outer envelope 46. The embodiment illustrated includes a proximal protrusion 52 and a distal protrusion 50, both shown extending in close proximity to vessel inner wall 23. Catheter 40 includes a combination perfusion-guide wire lumen 55.

Catheter 40 is shown containing a guide wire 54 within a guide wire lumen 56. Catheter 40 also includes an inflation lumen 58 and a compound application lumen 60. A preferred embodiment includes a radiopaque marker band 62. An estrogen inducing compound 64 is illustrated within lumen 60, within interior space 47, outside outer envelope 46, and in contact with vessel inner wall 23. Estrogen compound 64 is shown flowing between holes 45 in outer envelope 46 to vessel inner wall 23.

Figure 2:
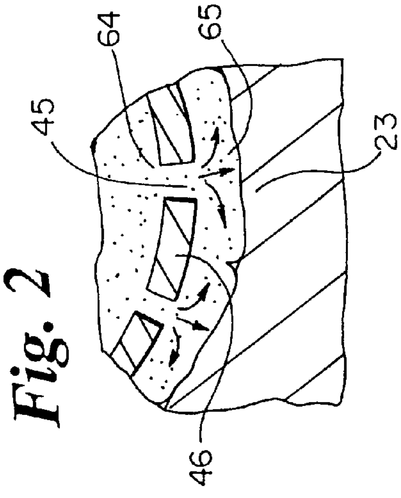
FIG. 2 is an enlarged sectional view of FIG. 1 taken along 2—2, illustrating estrogen compound flow from application device through outer envelope to the vessel wall.

FIG. 2 illustrates in greater detail estrogen compound 64 flowing at 65 through holes 45 in outer envelope 46 to vessel inner wall 23. The contours and spaces between the catheter balloon 43 and the vessel wall 23, along with the thickness of estrogen compound 64 are not drawn to scale in FIGS. 1 and 2, but rather illustrate the application of the present invention.

In use, guide wire 54 can be advanced through the vasculature and just proximal to or through stenosis 30. Delivery catheter 40 may then be threaded onto guide wire 54 and advanced to a position proximal to or upstream of stenosis 30. Once in place, inner balloon 43 can be inflated, causing outer balloon 46 to more closely approach or touch vessel wall 23. Estrogen compound 64 can then be injected into compound lumen 60, forcing the compound into interior space 47 and through holes 45 in porous outer balloon 46. A preferred method of delivery includes further pressurizing inner balloon 48 to force estrogen compound 64 against vessel inner wall 23. Another preferred method includes injecting compound 64 under pressure while inflation pressure is being supplied to balloon 48, applying estrogen compound 64 under pressure against vessel inner wall 23.

Preferred estrogen compounds include 17-Beta Estradiol., estradiol (E2) or estriol (E3).

Numerous characteristics and advantages of the invention covered by this document have been set forth in the foregoing description. It will be understood, however, that this disclosure is, in many respects, only illustrative. Changes may be made in details, particularly in matters of shape, size, and arrangement of parts without exceeding the scope of the invention. The inventions's scope is, of course, defined in the language in which the appended claims are expressed.

What is claimed is:

1. A method of increasing blood flow to ischemic tissue, comprising the steps of:

advancing a delivery device to a vascular site proximal of ischemic tissue; and applying an estrogen compound to the vascular site proximal of the ischemic tissue with resulting induction of angiogenesis at the vascular site.

2. A method of increasing blood flow to ischemic tissue as in claim 1, wherein the estrogen compound is delivered iontrophoretically.

3. A method of increasing blood flow to ischemic tissue as in claim 1, wherein the delivery device comprises a stent.

4. A method of increasing blood flow to ischemic tissue as in claim 3, wherein the estrogen compound is coated on the stent.

5. A method of increasing blood flow to ischemic tissue as in claim 4, wherein the stent is a temporary stent.

6. A method of increasing blood flow to ischemic tissue as in claim 4, wherein the stent is a permanent stent.

7. A method of increasing blood flow to ischemic tissue as in claim 1, wherein the delivery device comprises a drug delivery catheter.

8. A method of increasing blood flow to ischemic tissue as in claim 7, wherein the drug delivery catheter includes a pourous balloon, further comprising the step of delivering the estrogen compound through the pourous balloon.

9. A method of increasing blood flow to ischemic tissue as in claim 7, wherein the drug delivery catheter includes a catheter lumen, an inner balloon and a pourous balloon surrounding the inner balloon, further comprising the steps of:

inflating the inner balloon such that the pourous balloon comes into contact with a vascular wall at the vascular site; and injecting the estrogen compound between the inner and pourous balloons by way of the catheter lumen such that the estrogen compound exits the pourous balloon and is applied to the vascular wall.

10. A method of increasing blood flow to ischemic tissue as in claim 7, wherein the drug delivery catheter includes a balloon having the estrogen compound coated thereon, further comprising the step of inflating the balloon such that the estrogen compound is forced against a vascular wall at the vascular site.

11. A method of increasing blood flow to ischemic tissue as in claim 7, wherein the drug delivery device includes a puncturing element, further comprising the steps of:

moving the puncturing element into puncturing position;

puncturing an inner vascular wall at the vascular site; and injecting the estrogen compound into the vascular wall.

* * * * *